United States Patent
Patel et al.

(10) Patent No.: US 10,573,415 B2
(45) Date of Patent: Feb. 25, 2020

(54) SYSTEM FOR USING PATIENT DATA COMBINED WITH DATABASE DATA TO PREDICT AND REPORT OUTCOMES

(71) Applicant: Medtronic, Inc., Minneapolis, MN (US)

(72) Inventors: Amisha S. Patel, Apex, NC (US); Kenneth M. Riff, St. Louis Park, MN (US); Luc R. Mongeon, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 763 days.

(21) Appl. No.: 14/257,232

(22) Filed: Apr. 21, 2014

(65) Prior Publication Data

US 2015/0302178 A1   Oct. 22, 2015

(51) Int. Cl.
*G16H 50/70* (2018.01)
*G16H 40/20* (2018.01)
*G16H 50/50* (2018.01)
*G16H 50/20* (2018.01)
*G06F 19/00* (2018.01)

(52) U.S. Cl.
CPC ............. *G16H 50/70* (2018.01); *G06F 19/00* (2013.01); *G16H 40/20* (2018.01); *G16H 50/20* (2018.01); *G16H 50/50* (2018.01)

(58) Field of Classification Search
None
See application file for complete search history.

(56) References Cited

U.S. PATENT DOCUMENTS

| | | |
|---|---|---|
| 5,772,585 A | 6/1998 | Lavin et al. |
| 6,277,071 B1 | 8/2001 | Hennessy et al. |
| 6,336,903 B1 | 1/2002 | Bardy |
| 6,368,284 B1 | 4/2002 | Bardy |
| 6,440,066 B1 | 8/2002 | Bardy |
| 6,599,250 B2 | 7/2003 | Webb et al. |
| 6,804,656 B1 | 10/2004 | Rosenfeld et al. |
| 6,938,728 B2 | 9/2005 | Chae et al. |
| 7,165,221 B2 | 1/2007 | Monteleone et al. |
| 7,292,139 B2 | 11/2007 | Mazar et al. |
| 7,299,087 B2 | 11/2007 | Bardy |
| 7,426,475 B1 | 9/2008 | Tangellapally et al. |

(Continued)

FOREIGN PATENT DOCUMENTS

| | | |
|---|---|---|
| WO | 2001048672 A2 | 7/2001 |
| WO | 2013016143 A1 | 1/2013 |

*Primary Examiner* — Jonathan Ng
*Assistant Examiner* — Rachelle L Reichert
(74) *Attorney, Agent, or Firm* — Shumaker & Sieffert, P.A.

(57) ABSTRACT

A system and associated method receives, by a database coupled to a communication network, patient medical data from multiple data sources including data retrieved from implantable medical devices implanted in patients. A processor accesses the database to generate a dataset from the medical data having at least one data characteristic matching a corresponding data characteristic of a patient group of at least one patient. At least one subset of the dataset is identified that had a therapy intervention subsequent to a time point that the subset had the matching data characteristic(s). An outcome of the subset is determined and a predictive outcome for the patient group is produced based on the outcome of at least one subset.

24 Claims, 9 Drawing Sheets

(56) References Cited

U.S. PATENT DOCUMENTS

| | | | |
|---|---|---|---|
| 7,539,539 B1* | 5/2009 | Bharmi | A61B 5/0452 600/529 |
| 7,752,060 B2 | 7/2010 | Hicks et al. | |
| 7,818,180 B2 | 10/2010 | Riff | |
| 7,831,444 B2 | 11/2010 | Brown et al. | |
| 8,290,791 B2 | 10/2012 | Patel et al. | |
| 2001/0051787 A1* | 12/2001 | Haller | A61B 5/0031 604/66 |
| 2002/0026103 A1* | 2/2002 | Norris | A61B 5/0031 600/300 |
| 2002/0082480 A1* | 6/2002 | Riff | G06F 19/3418 600/300 |
| 2004/0172302 A1* | 9/2004 | Martucci | A61B 5/0002 705/2 |
| 2005/0204310 A1 | 9/2005 | De Zwart et al. | |
| 2005/0261941 A1* | 11/2005 | Scarlat | G06Q 50/24 705/3 |
| 2006/0031094 A1* | 2/2006 | Cohen | A61M 5/1723 705/2 |
| 2006/0064020 A1 | 3/2006 | Burnes et al. | |
| 2006/0074462 A1 | 4/2006 | Verhoef | |
| 2006/0218010 A1* | 9/2006 | Michon | G06F 19/345 705/3 |
| 2008/0058884 A1* | 3/2008 | Matos | A61N 1/37282 607/30 |
| 2008/0097912 A1* | 4/2008 | Dicks | G06Q 50/24 705/50 |
| 2008/0097913 A1* | 4/2008 | Dicks | G06Q 50/24 705/50 |
| 2008/0161700 A1* | 7/2008 | Sachanandani | A61B 5/0205 600/481 |
| 2008/0162182 A1* | 7/2008 | Cazares | G06Q 50/22 705/2 |
| 2008/0162183 A1* | 7/2008 | Sachanandani | G06F 19/345 705/2 |
| 2008/0306764 A1* | 12/2008 | Weiss-Meilik | G06Q 30/02 705/2 |
| 2008/0319781 A1* | 12/2008 | Stivoric | G06F 17/30598 705/2 |
| 2009/0063193 A1* | 3/2009 | Barton | A61N 1/37282 705/3 |
| 2009/0125328 A1* | 5/2009 | Nevins | G06Q 50/24 705/3 |
| 2009/0156908 A1 | 6/2009 | Belalcazar et al. | |
| 2009/0234672 A1 | 9/2009 | Dicks et al. | |
| 2009/0292340 A1 | 11/2009 | Mass et al. | |
| 2010/0113890 A1 | 5/2010 | Cho et al. | |
| 2010/0211135 A1 | 8/2010 | Caparso et al. | |
| 2011/0208012 A1 | 8/2011 | Gerber et al. | |
| 2012/0245953 A1* | 9/2012 | Morris | G06Q 10/10 705/2 |
| 2012/0253207 A1* | 10/2012 | Sarkar | G06F 19/3431 600/483 |
| 2013/0024207 A1* | 1/2013 | Anderson | G06F 19/322 705/3 |
| 2013/0232103 A1 | 9/2013 | Saeed | |
| 2015/0032467 A1* | 1/2015 | Rapp | G06Q 10/0639 705/2 |

* cited by examiner

SYSTEM FOR USING PATIENT DATA COMBINED WITH DATABASE DATA TO PREDICT AND REPORT OUTCOMES

TECHNICAL FIELD

The disclosure relates to a system and associated method for using individual patient data and clinical database data to report outcomes.

BACKGROUND

A variety of commercially available implantable medical devices (IMDs) are available, which collect physiological signals from sensors and extract and store data from those signals. These IMDs are often capable of delivering therapies and storing data relating to the success of those therapies. Examples of such IMDs include pacemakers, implantable cardioverter defibrillators (ICDs), cardiac monitors, neurostimulators, and drug pumps.

Expanding clinical databases receive IMD data from patients through networked remote patient monitoring systems. An ever-growing amount of data pertaining to individual patients and patient populations is stored in these databases. Clinicians strive to make the best treatment decisions possible for an individual patient. Yet many programmable parameters exist in a given IMD, sometimes more than one hundred programmable parameter settings may be available. Determining optimal operating parameters of a programmable IMD can be a time-consuming task. Selecting optimal IMD operating parameters is among many other treatment options a clinician may have, including prescription medications and surgical interventions. Since knowledge and understanding of medical conditions and the mechanisms of benefit of relevant therapies is always evolving, the best medical practices for treating a patient may be dynamic and difficult to ascertain from an individual patient or small group of patients.

Current medical database systems make individual patient data available to authorized users. The vast amount of data stored in medical databases, however, may be an under-used source of valuable information that could help clinicians develop and improve best practices for treating a wide variety of patients.

SUMMARY

In general, the disclosure is directed toward generating outcomes reports using data accumulated in a medical database for use in predicting therapy intervention outcomes and cost of medical treatment for a group of one or more patients. In one embodiment, a medical device system includes a centralized database coupled to a communication network. The database is configured to store data received via the network from a plurality of data sources including data retrieved from implantable medical devices implanted in patients. A centralized computer or other processor coupled to the database via the network is configured to compare data of a selected patient group of one or more patients to data stored in the database to identify patient records stored in the database having matching data characteristics at some point in time to the selected patient group's current data characteristics. Selected data characteristics may be searched for among all the patient records stored in the database. The patient records identified that have the selected data characteristics that match the patient group under evaluation are referred to herein as a "matching dataset."

The centralized computer or other processor separates the matching dataset into subsets according to different therapy interventions or patient care practices. For example, the centralized computer may sort the matching patient records according to therapy interventions that occurred subsequent to a time point that a given patient record had the matching data characteristics to the patient group. These subsets may be referred to as "interventional" subsets. An outcome for each interventional subset is determined. The centralized computer produces an outcomes report for the selected patient group based on the actual outcome of each interventional subset. In some examples, the actual outcome of each therapy intervention subset is reported as a predictive outcome for the selected patient group. A remote computer coupled to the network may be configured for receiving and displaying the outcomes report for use by a clinician or other authorized user.

The details of one or more aspects of the disclosure are set forth in the accompanying drawings and the description below. Other features, objects, and advantages will be apparent from the description and drawings, and from the claims.

DETAILED DESCRIPTION

Figure 1:
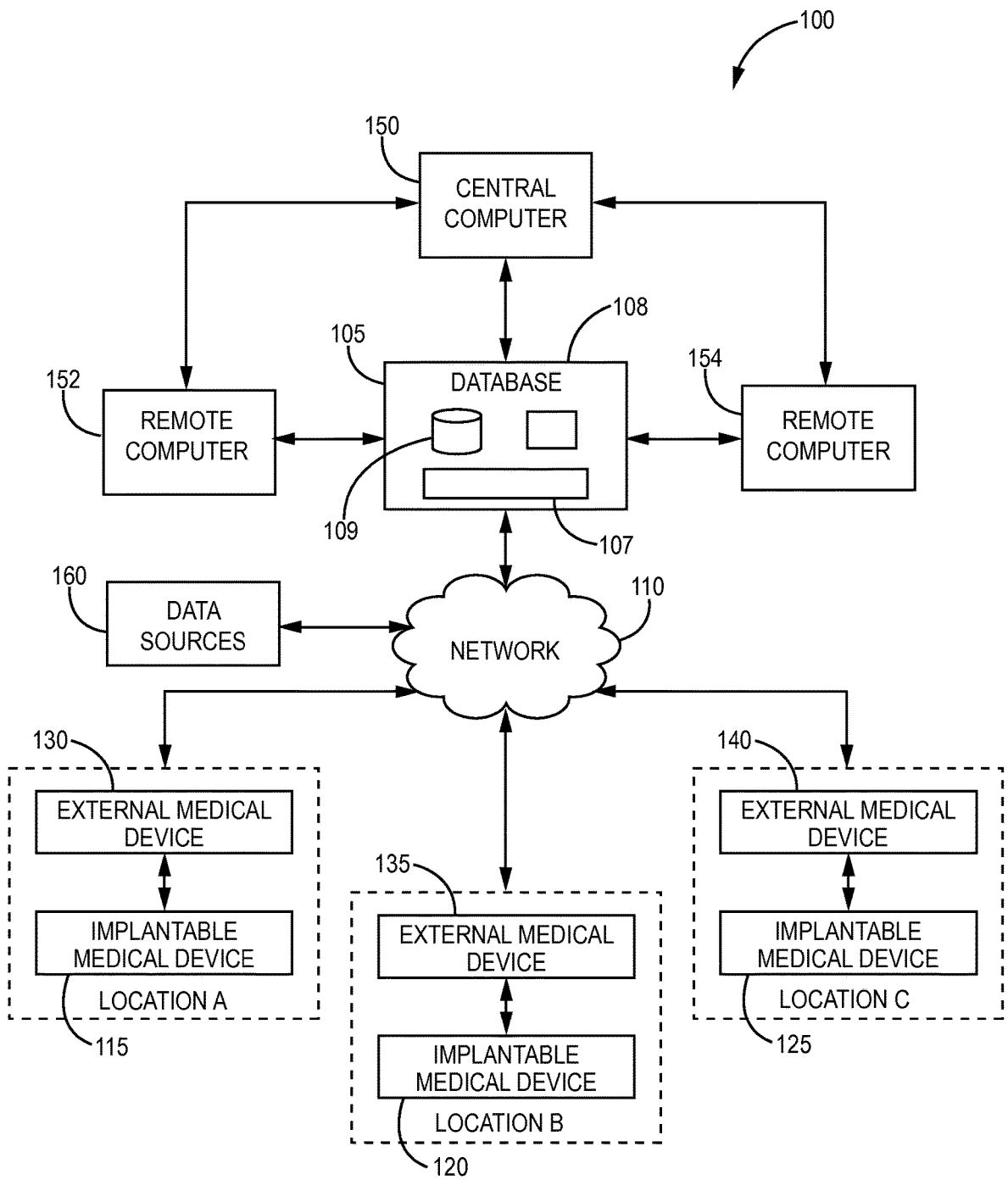
FIG. 1 is a schematic diagram of one embodiment of an implantable medical device (IMD) system.

FIG. 1 is a schematic diagram of one embodiment of a system 100 for accumulating patient data and generating outcomes reports. The following detailed description is illustrative in nature and is not intended to limit the scope, applicability, or configuration of the disclosed system in any way. Rather, the following description provides practical illustrations for implementing embodiments of a system for reporting outcomes using individual patient data in combination with broader medical database data.

In various embodiments, the system collects and analyzes patient data and provides predictive outcomes reports on an individual patient or a group of patients for review by a clinician or medical facility. Such systems include various equipment, as discussed herein, performing methods for accumulating data retrieved from IMDs, retrieved from external medical devices, entered by a clinician, retrieved from medical facility records, electronic medical records, and/or other sources. The system analyzes the data to identify a historical dataset matching a current patient or group of patients under evaluation. Outcomes within the matched dataset are reported as historical, i.e. actual, outcomes that are predictive of an outcome that could be reasonably expected for the individual patient or group of patients under evaluation.

A selected patient group for which an outcomes report is generated may be an individual patient, a group of two or more patients treated by a clinician, or a group of patients being treated at a medical facility or group of facilities. Accordingly, the outcomes report may be used to guide therapy decisions for improving outcomes for an individual patient and/or improving overall outcomes achieved by an individual clinician or medical facility.

A wide variety of types of outcomes can be reported and generally can be classified as device-related outcomes, patient-related outcomes, and cost-related outcomes. The reported historical outcomes may include a frequency of events such as morbidity, mortality, events requiring therapy by the IMD, events requiring emergency care, events requiring doctor visits, device replacement, or other events relating to the patient or group of patients under evaluation. The historical outcomes may be reported as a value of or change in a physiological parameter or index used to monitor disease status or severity. The historical outcomes reported may include an economic analysis that computes or estimates medical costs for treating or managing a medical condition in historical a historical dataset to predict likely medical costs for treating an individual patient or a group of patients when the same or similar treatment actions or interventions are taken. Other examples of reported outcomes are described herein. In some examples, the reported outcomes, whether device-related, patient-related, or cost-related, are determined subsequent to a therapy intervention taken in a subset of patients that had data characteristics at some point in time that match current data characteristics of the patient group being evaluated.

A "therapy intervention" as used herein may refer to, without limitation, implantation of an automated medical device, reprogramming of the implantable device, replacement of the implantable device, adjustments to algorithms or protocols performed by an automated external device in communication with a patient's implantable device, a surgical procedure, introduction or a change in a prescribed dosage of a prescription or non-prescription drug or supplement, a change in patient care practices such as a change in patient education, patient follow-up scheduling, a patient assessment performed by a specialist, or other patient care-related practices that alter a patient-related, device-related or cost-related outcome.

The remote patient management system 100 shown in FIG. 1 forms part of a system used for managing patients prescribed with medical monitoring or therapy delivery devices. System 100 includes a centralized computer 150 and database 105 coupled to a communication network 110. System 100 is used for accumulating data for use in predicting outcomes as will be described herein. System 100 may additionally be used to remotely program IMDs 115, 120 125 by transmitting code or commands back to IMD 115 received from an authorized user via a remote computer 152, 154.

Remote computers 152 and 154 may send requests and receive reports from the centralized computer 150 and database 105. Remote computers 152,154 may be computers located in hospitals, clinics, doctors' offices or other medical facilities. A clinician using a remote computer 152, 154 may request data and reports for a specific patient or group of patients the clinician is authorized to access. As will be described herein, the clinician or another user may request an outcomes report that presents information that is predictive of outcomes for an identified group of one or more patients based on actual outcomes in patient's for which data is accumulated in the central database 105 but are de-identified in the report. The algorithms and processes performed for generating a predictive outcomes report may be performed by the centralized computer 150 or by remote computer 152 or another external medical device 130, 135,140 after receiving appropriate data from the database 105. The algorithms and processes performed to generate the outcomes report may be performed by a processor included in central computer 150, remote computer 152, 154, or external medical devices 130, 135, 140 or any combination thereof.

Central database 105 receives individual patient data via network 110 from numerous external medical devices 130, 135, 140. The external medical devices 130, 135, 140 may be located in patient homes, doctors' offices, clinics, hospitals, emergency rooms, or other medical facilities. The external medical devices 130, 135 and 140 are configured to communicate with implantable medical devices (IMDs) 115, 120 and 125 to retrieve data acquired and stored by the IMDs or to retrieve physiological signals in real time, such as ECG signals, intracardiac electrogram (EGM) signals or blood pressure signals. In this way, a clinician or other authorized user can view patient data using a remote computer 152, 154 that has received the patient data transferred to the central database 108 via the network 110 from external medical devices 130, 135, 140 and IMDs 115, 120, 125. Patients may be located at a variety of distributed locations without having to make appointments and visit a medical facility. In various embodiments, central database 105 may be a database for storing data for an individual clinic, multiple clinics, a hospital, a hospital system, a geographical region, fully aggregated national data, or international data.

While only two remote computers 152, 154 and three external medical devices 130, 135, 140 and associated IMDs 115, 120, and 125 are shown, it is to be understood that system 100 may include a large number of external medical devices distributed at various geographic locations for receiving data from at least as many or more IMDs. Likewise, a large number of clinicians or medical facilities may be coupled to the database 105 via remote computers. The schematic diagram shown in FIG. 1 is not intended to convey any limitations of the number or locations of remote computers, IMDs, and external medical devices that may be in communication with central database 105 via network 110. Furthermore, many different kinds of clinicians or other authorized users may interact with the system 100. Various authorized users may include cardiologists, electrophysiologists, surgeons, neurologists, endocrinologists, heart failure specialists, and others.

Central database 105 includes a central communication module 107, which allows the database 105 to communicate with other system components. The central communication module 107 enables database 105 to provide information, such as instructions to medical devices at multiple patient locations or reports to clinicians or other users at multiple locations remote from the patient. Database 105 interacts with various types of equipment at each location through network 110. The network 110 can be a local area network (LAN), a wide area network (WAN), or other suitable telecommunications network, including the Internet. Database 105 may include a processor 108 for executing stored instructions for performing database operations, such as sorting and storing accumulated data in memory 109. Memory 109 can include electronic medical records from various data sources 160 and IMDs 115, 120 125 in a relational database and can include data files and code used for controlling communication with external components.

Database 105 may receive data only from implantable devices, e.g. IMDs 115, 120, 125, in some examples but may receive data from multiple other sources 160, which may include electronic medical records from clinics and hospitals, other monitoring devices, data entered by a patient or clinician, etc. Data for each patient represented in the database may be acquired from numerous sources other than the IMD implanted in the patient.

IMDs 115, 120, 125 may represent a cardiac stimulation device (e.g., a pacemaker or ICD), a cardiac monitor, a hemodynamic monitor, a neurostimulator, a drug delivery device, a glucose monitor, or other type or types of IMDs. The IMDs 115, 120, 125 at one location can be the same as or different than the IMDs 115, 120, 125 at other locations. The external medical devices (EMDs) 130, 135, 140 can be remote home monitors, programmers, or other EMDs configured to communicate with the IMD. The EMDs 130, 135, 140 retrieve various physiological data and device-related data from the IMDs 115, 120, 125. The EMDs 130, 135, 140 at one location can be the same or different than the EMDs 130, 135, 140 at the other locations. The IMDs 115, 120, 125 and/or the EMDs 130, 135, 140 can include some or all of the programmable options that are resident in the database 105.

EMDs 130, 135 and 140 may additionally be configured to receive patient or clinician entered data such as patient body weight, symptoms, patient activity logs, patient dietary logs, results of physical examinations or laboratory tests, prescriptions, or other medical data. Additionally or alternatively, patient data or associated medical records other than data acquired by and retrieved from IMDs 115, 120 and 125 can be entered by a clinician or other authorized user via remote computers 152,154 and transferred to central database 105.

Central computer 150 may be located in the same location as database 105 or remotely from database 105. Central computer 150 can be a device, or multiple devices working together, that accepts information (in the form of digitalized data) and manipulates it for some result based on a program or sequence of instructions on how the data is to be processed. In some embodiments, the computer 150 may include storage for storing data for some necessary duration. As described further herein, computer 150 may execute instructions for sorting, classifying, matching, and/or modeling data for determining matching datasets and using historical outcomes from a matching dataset for predicting outcomes for a given patient or group of patients if one or more therapy-related actions are taken.

The content of the information being communicated between the database 105, EMDs 130, 135, 140, IMDs 115, 120, 125, central computer 150, and remote computers 152, 154 varies according to the particular application. In some embodiments, the data may be focused data pertaining to a single medical condition or therapy indication and in other embodiments the data may be broader, including all patient medical history available from remote computers 152, data sources 160, IMDs 115, 120, 125, and EMDs 130, 135, 140. IMDs 115, 120, 125 can gather and/or store device-related data and patient-related data.

Examples of device-related data include programmed therapy delivery parameters, frequency and types of delivered therapies, programmed event detection and event discrimination parameters used for triggering or otherwise controlling therapy delivery, and device self-diagnostic data such as medical lead impedance and status and battery status. Examples of patient-related data includes physiological signals or metrics thereof used to indicate heart rhythm including arrhythmias, blood pressure, respiration, patient activity level, edema or body fluid status, heart wall motion, blood chemistry, and the like.

Data may be transmitted between IMD 115, 120, 125, remote computer 152, 154 and database 105 at any desired frequency for dynamically updating a patient status, dynamically updating a matching dataset or model, and updating historical outcomes of a subset of a matching dataset. The database 105 can index data received from the IMDs 115, 120, 125 according to patient, transmission date, IMD serial number, and/or any other factor that would aid in being able to access the data at a later date. Data may be accumulated in database 105 in a substantially ongoing manner as patient data is collected, retrieved and transmitted from a relatively large population of distributed patients. For example, database 105 may be receiving data from multiple sources on an hourly or daily basis since different patients may be on varying schedules for retrieving data from their IMDs.

Figure 2:
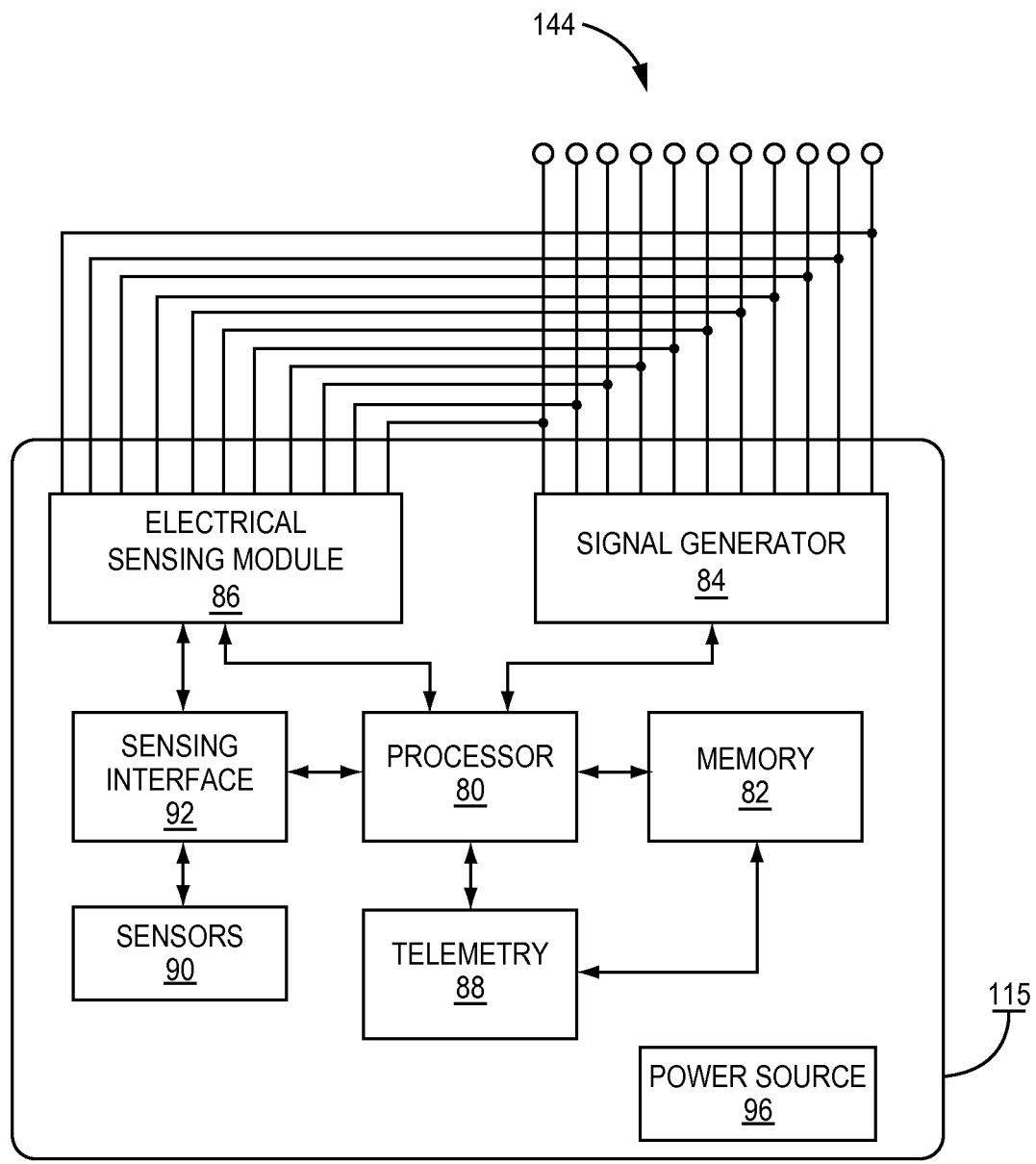
FIG. 2 is a functional block diagram of an example configuration of an IMD 10, which may be any of the IMDs 115, 120 or 125 shown in FIG. 1.

FIG. 2 is a functional block diagram of an example configuration of an IMD 10, which may be any of the IMDs 115, 120 or 125 shown in FIG. 1. In the example illustrated by FIG. 2, IMD 10 includes a processor and control module 80, also referred to herein as "processor" 80, memory 82, signal generator 84, electrical sensing module 86, and telemetry module 88. Electrical sensing module 86 is coupled to a number of electrodes 144 for sensing electrical signals, such as intracardiac electrogram (EGM) signals, subcutaneous ECG signals, or other nerve or electromyogram signals. Signal generator 84 is coupled to electrodes 144 for delivering electrical stimulation therapies, such as cardiac pacing, cardiac defibrillation or cardioversion shocks, or neural stimulation. Switching circuitry may be included in sensing module 86 and/or signal generator 84 to electrically couple selected electrodes 144 to sensing module and signal generator 84 as needed for sensing electrical signals and delivering electrical stimulation therapies.

IMD 10 may additionally include one or more physiological sensors 90, which may include a pressure sensor, pH sensor, temperature sensor, acoustical sensor, flow sensor, oxygen sensor, patient activity sensor or any other sensor used for producing a signal responsive to a time-varying physiological condition. Sensors 90 are shown schematically within IMD 10, however it is recognized that sensors 90 may alternatively be carried by a lead extending from IMD 10, mounted along the IMD housing, or positioned within or along a medical lead connector block.

Modules 80, 84, 86, 88, 92, memory 82, and sensors 90 shown in FIG. 2 may include any discrete and/or integrated electronic circuit components that implement analog and/or digital circuits capable of producing the functions attributed to and IMD herein. For example, sensing module 86, sensing interface 92, and processor and control module 80 may include analog circuits, e.g., amplification circuits, filtering circuits, and/or other analog circuitry for receiving and processing signals from electrodes 144 and sensors 90. Sensing module 86, sensing interface 92 and processing and control module 80 may also include digital circuits, e.g., combinational or sequential logic circuits, memory devices, ND converters, etc. for processing received signals.

The functions attributed to an IMD as disclosed herein may be embodied as one or more processors, hardware, firmware, software, or any combination thereof. Depiction of different features as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components.

Sensing interface 92 is configured to receive one or more analog signals from electrical sensing module 86 and sensors 90. Sensing interface 92 includes an ND converter for converting analog signals to digital signals. Processor 80 receives the converted digital signals and may analyze the digital signals for detecting a patient event, controlling a therapy delivered by signal generator 84, and/or storing patient data in memory 82 for later transmission via telemetry module 88. Processor 80 may receive analog signals directing from sensing module 86 and sensors 90 for detecting events. For example, processor 80 may be configured to detect arrhythmias and control signal generator 84 to deliver cardiac pacing and/or cardioversion defibrillation therapies based on signals received from sensing module 86 and sensors 90.

A power source 96 provides power to each of the other modules and components of IMD 10 as required. Processor 80 may execute power control operations to control when various components or modules are powered to perform various IMD functions. Power source 96 may include one or more energy storage devices, such as one or more rechargeable or non-rechargeable batteries. Processor 80 may also be configured to perform diagnostic testing of IMD 10, which may include monitoring the remaining charge of power source 96 and providing an elective replacement or recharge indicator, for example. The connections between power source 96 and processor 80 and other IMD modules and components are not shown for the sake of clarity.

Memory 82 may include computer-readable instructions that, when executed by processor 80, cause IMD 10 and processor 80 to perform various functions attributed throughout this disclosure to an IMD. The computer-readable instructions may be encoded within memory 82. Memory 82 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Processor and control module 80 may include any one or more of a microprocessor, state machine, a controller, a digital signal processor (DSP), an application specific integrated circuit (ASIC), a field-programmable gate array (FPGA), or equivalent discrete or integrated logic circuitry. Processor and control module 80 includes a therapy control module that controls signal generator 84 to deliver electrical stimulation therapy according to a selected one or more therapy programs, which may be stored in memory 82.

Telemetry module 88 includes an antenna and transceiver for wireless transmission of data to and receiving commands from an external medical device 130, 135, 140. Telemetry module 88 may communicate using radio frequency signals in a MICS, MEDS or other communication band. Telemetry module 88 may be configured to communicate with an external medical device via inductive coupling, electromagnetic coupling, tissue conductance, Near Field Communication (NFC), Radio Frequency Identification (RFID), BLUETOOTH® Low Energy or other proprietary or non-proprietary wireless telemetry communication schemes. The communication techniques used to acquire data from an IMD in system 100 may vary between location, device type, etc.

Figure 3:
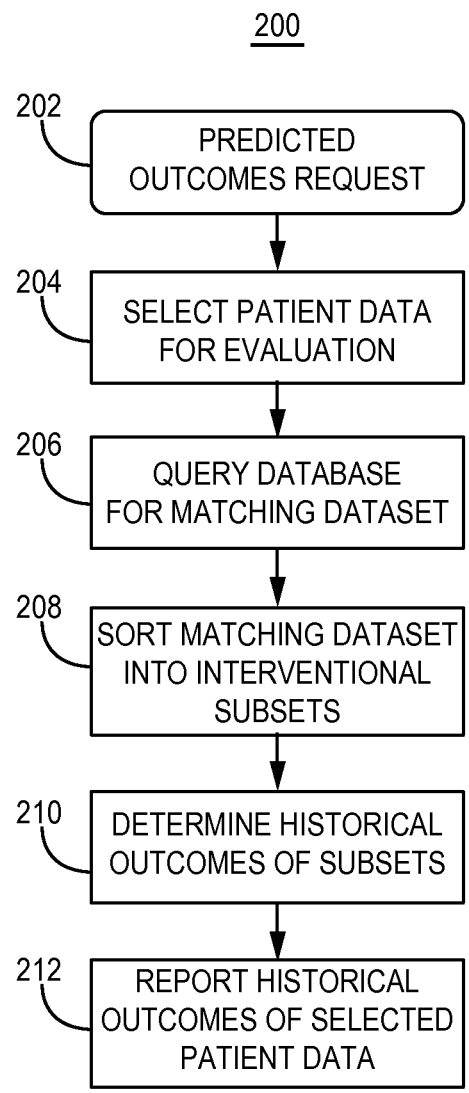
FIG. 3 is a flow chart of a method performed by the system shown in FIG. 1 according to one embodiment.

FIG. 3 is a flow chart 200 of a method performed by system 100 according to one embodiment. Database 105 and central computer 150 may be configured to execute instructions for performing the method shown by flow chart 200, with input received from other system components as needed. The functionality described herein may be distributed across one or more computers or processors accessing one or more computer-readable storage media.

A request for a predicted outcomes report is generated at block 202. A clinician may request a predicted outcomes report using a remote computer 152, 154 in communication with database 105. The clinician or other authorized user may request a report for a single patient the clinician is treating or a group of patients being treated by the clinician or an associated medical facility. For example, the clinician may request that multiple patients implanted with a particular type or model of IMD, such as a pacemaker or ICD, being followed-up by a given medical center be evaluated for predicted outcomes.

Instead of a manual request, a predicted outcomes request may be generated automatically at block 202, e.g. on a scheduled basis for a given clinician or authorized user or a given medical facility. For example, a predicted outcomes report may be generated on a periodic basis, such as weekly, monthly, semi-annually, annually or otherwise, for all patients identified as being treated by a particular clinician and the reports may be bundled and transferred to a remote computer 152, 154 for access by the clinician. Individualized reports (pertaining to a specific patient) and/or group reports (pertaining to a group of patients having a common diagnosis, IMD, medical condition, clinician, and/or follow-up medical facility) may be requested. Accordingly, when a request is made, specific parameters used for generating an outcomes report may be specified by a user.

The central database 105 and computer 150 may provide a service to a clinician or medical facility by producing updated predicted outcomes reports without receiving a manual request. For example, a predicted outcomes report may be generated as more data is accumulated in the central database 105. Central database 105 and computer 150 may regularly perform outcomes analysis as data is accumulated and when a predicted outcome changes from a previous report for a given patient or medical facility. A new report is produced when a predicted outcome changes. A predicted outcome may change due a change in the data characteristics of a patient causing the patient to no longer match a previous group of patients and/or because the outcomes of a therapy subset of a matching group of patients has changed. Accordingly, a predicted outcomes request may be generated at block 202 in a variety of ways including, but not limited to, a manual request by an authorized user and automatic requests based on a periodic time interval, amount of newly accumulated data since a previous report, or changes in a predicted outcome since a previous report.

At block 202, data from the database 105 pertaining to the group of one or more patients to be evaluated are selected. In some examples, the data selected includes all available data stored in the database for a given patient or group of patients. Such data may include data retrieved from an IMD, from electronic medical records, and other sources. In other examples, a subset of all available data is selected. For example, a subset of data may be data spanning a particular time period. Data that is older than a certain date may not be selected. A subset of data may be data retrieved from a particular IMD model or type of IMD. For example, if a patient has more than one implanted device for treating more than one medical condition, selected data may be data retrieved from only one of the IMDs. Data stored in the database 105 may include data acquired from earlier models of a given device type, e.g. earlier pacemaker or ICD models. A subset of data may be selected from certain device models. A subset of data may include/exclude certain types of data based on clinical relevance to the evaluation being performed.

Data characteristics are determined from the selected data that are representative of the patient group being evaluated. The data characteristics may include programmed settings of an IMD, data relating to the frequency and/or types of therapies delivered by the IMD, parameters determined from physiological signals sensed by the IMD or other internal or external sensors including measurements, trends, and/or detected events or conditions, patient symptoms, etc.

At block 206, a query of the database 105 is performed to search for patient records that match the patient group selected for evaluation. The matching dataset is identified based on at least one data characteristic. A matching dataset may be identified based on a single data characteristic, e.g. type of IMD implanted or diagnosis. In other examples, the matching dataset may include multiple data characteristics such as device type, diagnosis, and physiological markers or indices.

In an example of a single patient being evaluated, the database may be queried for all other patients that at some point in time had the same or similar data characteristics as the patient. These data characteristics may be related to the detection of particular events or conditions. For example, a patient group under evaluation may have heart rhythm data characterized by particular rate(s), arrhythmia episode frequency, arrhythmia burden, pacing burden, frequency of anti-arrhythmia or shock therapies, etc. The database is queried for all patients that had matching characteristics at some point in time to the data characteristics of the patient group at the present time. Matching characteristics may be exact matches but not necessarily and may be matches within a given range of the data under evaluation.

Other types of data that may characterize a patient group under evaluation may relate to a heart failure condition. For example, such data may include indicators of systolic pressure, diastolic pressure, heart rate, activities of daily living, ejection fraction, cardiac output, cardiac conduction times, a percentage of time a cardiac resynchronization therapy is being delivered to one or both ventricles, prescribed medications, echocardiography results, stress testing results, etc. Patient records stored in the central database that include the types of data stored for the patient(s) under evaluation and substantially match the data under evaluation are identified by the central computer 150. The matching dataset may include patient records identified from any point in time and do not need to be records that were accumulated within a given time range. However in some embodiments, the query may be limited to a specified date range, for example to eliminate interventions that may not be relevant to newer implantable device models or other advances in medical practice.

At block 208, the matching dataset identified at block 206 is sorted based on therapy interventions. Therapy interventions that took place subsequent to the time that a given dataset matched the data characteristics of the patient group undergoing evaluation are identified and used to sort the matching dataset into subsets. Examples of therapy interventions have been listed above and may include a programming change made to an IMD or a device in communication with the IMD, a prescription drug change, surgery, or other doctor prescribed intervention.

An intervention that is a programming change to an IMD may be a change to a therapy control parameter or a detection control parameter used by the IMD to deliver a therapy or detect a condition or event, respectively. A programmable change may be turning a feature "ON" or "OFF" in the IMD or adjusting a parameter value used to control therapy delivery or event detection operations. An intervention may include changing one or more programmable parameters.

Therapy related programming changes are changes to therapy control parameters that alter the manner in which a therapy is delivered. For example, a therapy may be turned ON or OFF or a different type of therapy may be selected to be delivered. A therapy that is already enabled may be adjusted in rate, frequency, intensity or in another manner depending on the particular therapy.

Detection related programming changes are changes to detection control parameters that alter how a condition or event is being detected, which may or may not result in a therapy delivery. For example, thresholds or other criteria may be adjusted for detecting a condition or event. Sensor signals available for use in detecting a condition or event may be added or removed from a detection algorithm. Weighting factors or hierarchical rules for detecting a condition may be adjusted. One or more detection features may be turned ON or OFF. For example, features for discriminating ventricular and supraventricular arrhythmias may be turned on or off based on a clinician preference, patient need or other reasons.

Adjustments or changes to external devices communicating with the IMD may also be made. Examples of changes to an external device may include a change in protocols for retrieving data from the IMD, e.g. the frequency or type of data retrieved from the IMD and a change in how alerts or notifications are generated by the external device, e.g. when and where the alert is sent. These and other changes to the operation of an external device configured to communicate with the IMD may influence a patient-related, device-related or cost-related outcome and are therefore considered to be therapy interventions that could be sorted into interventional subsets.

Other interventions identified among the matching datasets may include a prescription change, a surgery, or a device change if a new IMD is implanted, a new electrical lead or sensor implanted, or an IMD software update. Depending on the particular medical application, the number and type of possible interventions that may be identified in the matching dataset may vary.

After sorting the matching dataset into interventional subsets at block 208, the historical outcomes of the subsets are determined at block 210. Subsets may be required to have a minimum number of patients to be included in the outcomes report. For example, at least five patients or other minimum number of patients undergoing a given intervention may be required. If only one patient falls in an interventional subset, the subset may be ignored. A statistical correlation between an intervention and an outcome within an interventional group may be required to include the subset in the outcomes report. Alternatively, subsets having less than a threshold number of patients could be reported in an outcomes report as anecdotal results.

Outcomes may be patient-related outcomes and/or device-performance related outcomes. An outcome can be a change in a data characteristic that was used to identify a matching dataset. For example a frequency or percentage of time that a patient experiences a particular heart rhythm may have been used as a data characteristic for identifying the matching dataset and the characteristic may increase or decrease in an interventional subset subsequent to the intervention. A change in any of the data characteristics used to identify the matching dataset, including therapy delivery characteristics, characteristics derived from physiological sensors, characteristics derived from electronic medical records including symptoms, patient quality of life, or activities of daily living, could be determined as outcomes following an intervention.

Outcomes may additionally or alternatively be other measures, indicators or markers that were not used as a data characteristic for identifying the matching dataset. For example, patient-related outcomes may pertain to mortality, morbidity, patient well-being or general health or other measures of therapy effectiveness. Examples of device-related outcomes include the time to reach elective device replacement indicator, a number of unnecessary therapies delivered due to false event detections or a percentage of time or frequency that pacing or another therapy is delivered.

One or more outcomes may be determined at block 210 for each interventional subset. The outcomes may represent a percentage of the patients in the interventional subset that experienced an improvement in a patient- or device-related outcome. The number of patients represented by each interventional subset may also be reported. For example, the outcome of a particular intervention may be reported as X % (of Y patients) had a subsequent change in parameter Z. The change may be reported as a decrease or an increase and may or may not include an absolute or relative amount of change. For example, an outcome may be reported as X % of patients experienced at least a Y % increase in parameter Z. It is understood that the written manner in which the outcome is expressed may vary depending on the particular type of outcome or data being reported.

At block 212, an outcomes report is produced. The outcomes report may be transmitted to a remote computer at a medical facility where the patient or patient group under evaluation is being followed by one or more clinicians. The report includes historical outcomes for each of the interventional subsets. These historical outcomes provide predictive information for the clinician in making treatment decisions for the patient or group of patients under evaluation without necessarily giving direct therapy or treatment recommendations.

Figure 4:
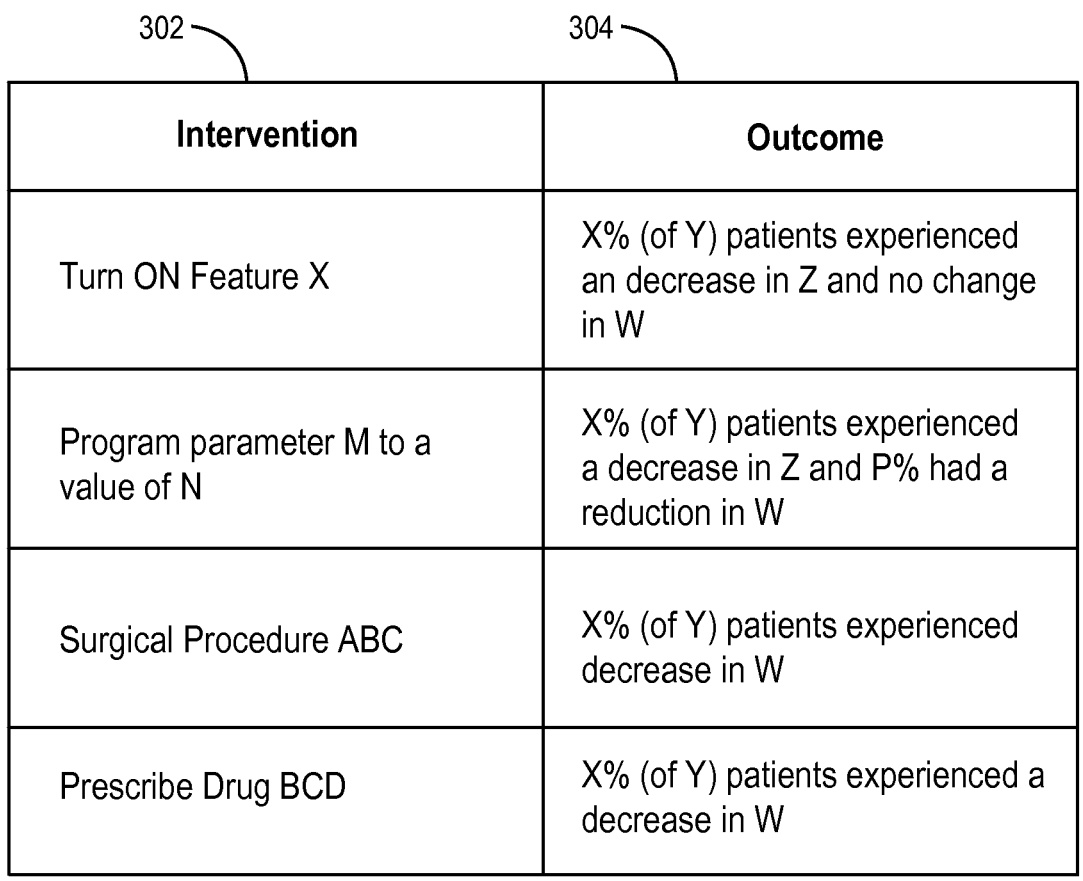
FIG. 4 is an illustration of information that could be included in an outcomes report displayed to a clinician.

FIG. 4 is an illustration of information that could be included in an outcomes report displayed to a clinician. The outcomes report may include a list of interventional subsets 302 and corresponding historical outcomes 304. The interventional subsets may be filtered in some embodiments to be limited to particular types of subsets, such as IMD programming changes only, prescription drug changes only, surgical interventions only, or any combination of subsets. In other examples, all subsets identified during the sorting performed at block 208 in FIG. 3, possibly with the exception of subsets not reaching a threshold number of patients or statistically significant results, may be included in the report. The report may be sortable or filterable in a user display to enable a clinician to view historical outcomes in a desired filtered, ordered or ranked display.

In the illustrative example shown, four interventional subsets are listed including: 1) turning ON an IMD Feature X, 2) programming parameter M to a value of N, 3) performing a surgical procedure "ABC," and 4) prescribing drug "BCD." An outcome 304 is reported for each intervention. In this hypothetical example, an outcome for turning ON Feature X of an IMD, an outcome is reported as X % (of Y) patients experienced a decrease in parameter Z with no change in parameter W.

In an illustrative example, a clinician may be treating a patient experiencing persistent atrial fibrillation and may be considering treatment options. The clinician may request an outcomes report for the patient. The central database and central computer perform the method shown by flow chart 200 to compare the patient's data characteristics, which may include current and historical data, to data characteristics of patients stored in the central database to identify a matching dataset. For example, the patient under evaluation may be experiencing persistent AF with a cycle length of 280 ms. Other data characteristics may include frequency of anti-tachycardia pacing therapy, frequency of shock therapies, or other rhythm information.

The central database and central computer identifies all patient records that at one time had the same data characteristics as the patient as a matching dataset. The matching dataset is sorted into the interventional subsets. In the illustrative example shown in FIG. 4, four interventional subsets may be found among all patients that at one time or another had persistent AF with a cycle length of 280 ms. The intervention "Turn ON Feature X" may correspond to turning ON an arrhythmia detection or discrimination feature, such as an AF discrimination rule, used by the IMD in performing an arrhythmia discrimination algorithm. The reported outcome may be that X % of patients that had the AF discrimination criteria turned ON had a decrease in inappropriate shocks due to false detections of AF as a ventricular tachyarrhythmia. There may be no change in the AF burden, i.e. the percentage of time the patient's heart rhythm is an AF rhythm.

The intervention "Program parameter M to a value of N" may correspond to an arrhythmia detection parameter or a therapy delivery parameter. For example, an arrhythmia detection parameter could be the interval set as a ventricular tachycardia interval or the number of ventricular tachycardia (VT) intervals required to detect ventricular tachycardia or fibrillation. The parameter could be a therapy delivery parameter such as a pacing timing interval, e.g., an AV or VA interval. In the hypothetical example, the reported outcome may be that X % of the patients having the parameter adjustment had a decrease in the number of inappropriate shocks and a reduction in the AF burden.

A surgical procedure "ABC" performed for treating AF might be atrial ablation. The percentage of patients experiencing a decrease in AF burden might be reported as the outcome. A prescribed drug "BCD" might be an anti-arrhythmia drug, and the reported outcome may be the percentage of patients experiencing a decrease in arrhythmia burden.

The clinician can compare the reported outcomes for the various interventional subsets. Based on the matching data characteristics and reported historical outcomes of the interventional subsets, the clinician can choose intervention(s) for the patient under evaluation with the knowledge of reasonable predictive outcomes for that patient based on the historical outcomes. An outcome display or report lists historical outcomes of interventional subsets, but because the subsets had matching data characteristics to the patient group under evaluation, the outcomes are useful as reasonable predictive outcomes for the patient group under evaluation if the same intervention is taken.

Figure 5:
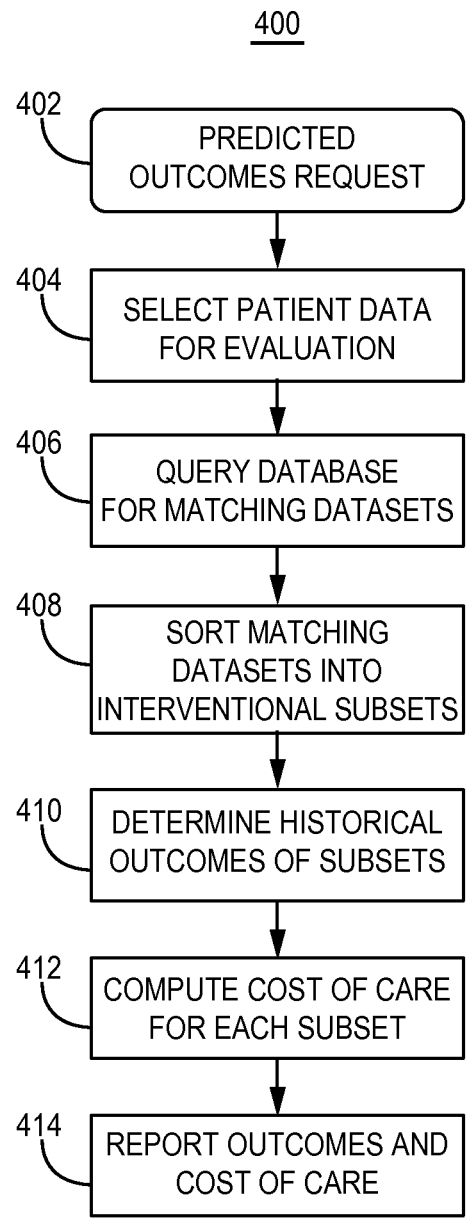
FIG. 5 is flow chart of a method for producing outcomes reports that include an economic analysis of the interventional subsets.

FIG. 5 is flow chart of a method for producing an outcomes report that includes an economic analysis of the interventional subsets. The outcomes report referred to in conjunction with FIG. 4 is primarily focused on patient-related and/or device-related outcomes, such as a change in AF burden and/or a change in the incidence of inappropriate shocks in the illustrative example provided. Another outcome that can be valuable to assess is the monetary cost of medical care. Some interventions may result in a reduction in office visit fees, hospitalization costs due to symptoms or complications, cost of prescription medicine or other medical testing, procedure or therapy costs. In addition to the cost of the intervention itself, a clinician or medical facility may be interested in how costs of medical care relating to a particular medical condition compare between interventional subsets subsequent to the interventions, and optionally including the cost of the intervention itself.

In the flow chart 400 of FIG. 5, the processes of generating an outcomes report request (block 402), selecting patient data for evaluation of a patient group (block 404), querying the database for matching patient records to generate a matching dataset (block 406) and sorting the matching dataset into interventional subsets (block 408) are performed as described previously. At block 410, patient-related and/or device-related outcomes subsequent to the intervention may be determined for each interventional subset as described above.

At block 412, an average cost of medical care is computed for each interventional subset. For each patient in a given subset, the cost of medical care subsequent to the intervention is determined from electronic medical records, for example. Costs of care subsequent to the intervention, including office visits, prescriptions, hospitalizations, laboratory tests or other diagnostic testing, may be summed. Costs may be summed from the time of the intervention until the current date or for a predetermined or specified time period following the intervention, e.g. one year. Costs may be reported as annualized costs over a given number of years or until the current date. Costs of medical care unrelated to the relevant medical condition may be excluded, such as non-related office visits.

In some embodiments, cost of care determined at block 412 may include costs incurred prior to the intervention. In this way, a determination may be made as to whether the cost of medical care is reduced compared to the cost of care prior to an intervention.

At block 414, an outcomes report is generated which may include the cost of care subsequent to the medical intervention and optionally compared to cost of care prior to the intervention. The cost of care may include the cost of the intervention itself such that a clinician or other user can evaluate the costs of performing a particular intervention and potential cost savings subsequent to the intervention in addition to predicted patient benefit. This information may guide a clinician or medical facility in making medical decisions that optimally benefit the patient while reducing or minimizing medical costs.

Figure 6:
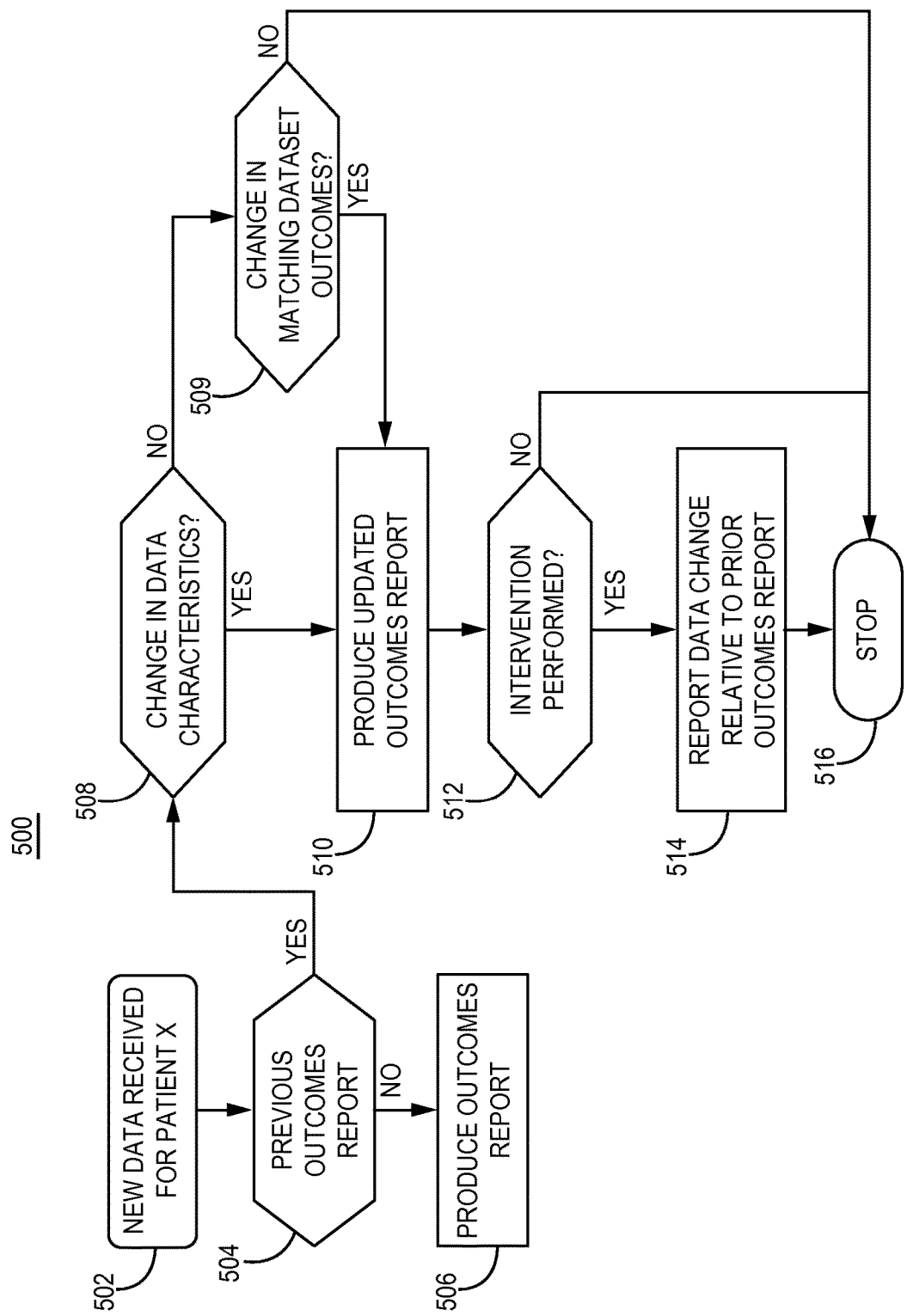
FIG. 6 is a flow chart of a method for generating predicted outcomes reports according to one embodiment.

FIG. 6 is a flow chart 500 of a method for generating predicted outcomes reports according to one embodiment. At block 502, new data for a patient is received by the central database. If the patient is a new patient to the database, or a previous outcomes report has not yet been generated (block 504), an outcomes report may be produced at block 506 as described above.

If a previous outcomes report exists (block 504), the central computer determines, at block 508, if there has been a change in the data characteristics for that patient since the last outcomes report was generated. If any of the data characteristics utilized in generating the last outcomes report have changed, a new outcomes report is produced at block 510. Since a previous report, a change in the patient's data characteristics may result in a different matching dataset from the database. Consequently, predicted outcomes based on actual outcomes of a matching dataset may change. The updated outcomes report produced at block 510, therefore, will be generated by first querying the database for a matching dataset as described previously. A newly identified matching dataset may or may not include patient records used to generate the previous outcomes report.

Since new data may be received by the central database on frequent and ongoing basis, the dataset and interventional subsets may be continuously evolving. An outcomes report may therefore be updated each time a patient's data characteristics change, but may also be updated without waiting for new data for a given patient group. Changes in the historic outcomes may occur as more data is added to the database for other patients, increasing the number of patient records matching the patient group under evaluation, increasing the number of patients in each interventional subset and/or increasing the number of subsets.

Accordingly, in some embodiments, as indicated at block 509, the central database may periodically determine if new data added to the database results in a change in the outcomes reported in the previous report for the patient group. The central database may generate a new outcomes report at block 510 based on changes in the database even if the data characteristics of the patient group under evaluation has not changed. Updated outcomes reports may be generated on a periodic basis and sent to a designated recipient whenever outcomes of interventional subsets change from a previous report.

If an intervention has been performed in the patient group since the previous outcomes report, as determined at block 512, the patient's new data characteristics may be compared to the previous report. If the patient underwent an intervention matching an interventional subset identified in the previous report, the patient's data characteristics could be compared to the interventional subset historical outcome to determine if the change in the patient's data characteristics meets or is approaching the expected outcome. The result of this comparison may be reported in the updated outcomes report at block 514.

Additionally or alternatively, the patient's current data characteristics may be compared to the current data characteristics of the interventional subset identified in the previous report. An indication of how the patient's response to the intervention compares to the current data characteristics of the matching interventional subset may be included in the updated report. For example, if a patient underwent a programming change since the previous outcomes report and experienced a decrease in data characteristic X, that outcome can be compared to the historical outcome of the interventional subset having the same programming change as well as the current data characteristic X for the interventional subset.

Figure 7:
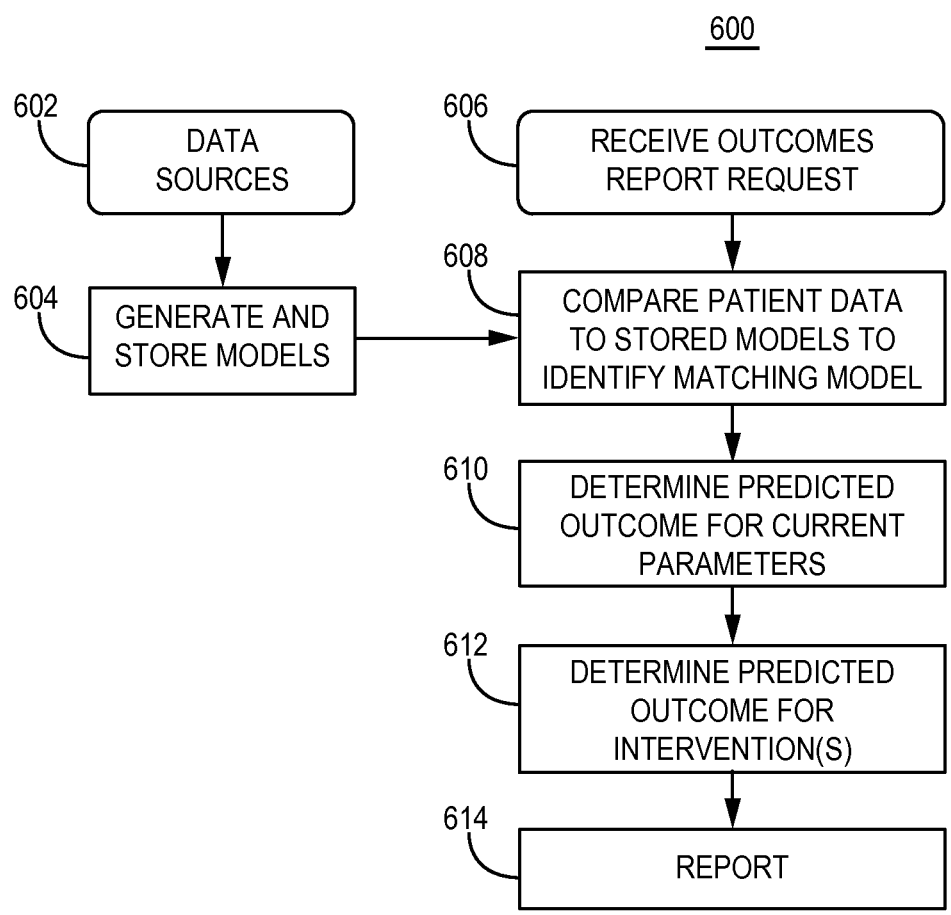
FIG. 7 is a flow chart of a method for producing a predictive outcomes report according to another example.

FIG. 7 is a flow chart of a method for producing a predictive outcomes report according to another example. At block 602, data from all available sources is accumulated in the central database. Available data sources may include electronic medical records and IMD data transmissions. The central computer generates mathematical models from the accumulated data at block 604. Mathematical models may be generated from data that represent patterns or clustering of the data characteristics. Multiple mathematical models of patient data can be produced to represent different categories or classifications of the patients.

Furthermore, a prediction or prognosis may be produced based on the modeling. For example, a mathematical model of a group of patients having similar data characteristics may predict a future probability of adverse events, such as tachyarrhythmia episodes, shock therapies, morbidity, mortality, reduction of a quality of life measure such as patient activity, elevated night heart rate, or other event or condition.

At block 606, an outcomes report request is received, which may be coincident with receiving new data for the patient group under evaluation. The patient data for which the report is requested is compared to stored models at block 608 to identify a best matching model. Accordingly, rather than querying the database for all patient records that match the patient group under evaluation at a given point in time, a stored mathematical model that best matches the patient group being evaluated is identified at block 608.

Using the stored model, a predicted outcome for the currently programmed IMD parameters is determined at block 610. This predicted outcome is what can be expected based on the model generated using the historical data stored in the central database if no change in IMD parameters or any other intervention is taken. A predicted outcome of one or more interventions may additionally or alternatively be determined at block 612 using the current patient data and the matching mathematical model. A predicted outcome may be an actual outcome of the mathematical model or a probability of a future event produced by the mathematical model.

In an illustrative example, data characteristics for the patient under evaluation may match a stored mathematical model relating to patients having atrial fibrillation. The patient's current settings for IMD programmable parameters may be used to predict how effective the current parameter settings are based on the matching model. In some examples, a reported outcome may include an updated prediction of how data characteristics of the patient are expected to change (or not change) if no intervention is taken. For example, if a patient's IMD remains at currently programmed settings, a patient may be expected to have a predicted percentage of false tachyarrhythmia detections, a predicted percentage of failed ATP therapies, a predicted occurrence of a shock therapy, or other outcome based on outcomes of matching models identified from the central database.

For example, the matching model may indicate an outcome of atrial anti-tachycardia therapy (ATP) that was successful only 2% of the time. This predicted outcome for currently programmed parameters may be determined at block 610. An increased time to elective replacement indicator may be an outcome that is determined at block 612 if the atrial ATP is turned off with no significant change in the number of ventricular tachyarrhythmias being detected or shock therapies delivered.

In another example, the ATP therapy may be turned off in the patient's IMD. A matching mathematical model, however, may indicate an 85% success rate of ATP. A predicted outcome of reduced shock delivery may be determined at block 612 if ATP is programmed ON in the patient group under evaluation. In these examples, a clinician can make an informed decision regarding whether ATP therapy should be programmed ON or OFF based on a predicted outcome for the patient group determined from the matching model.

By utilizing continuously updated data from the central database to determine historical outcomes of a matching dataset or matching mathematical model derived from historical data, best practices for managing a given type of patient can be determined as patient management strategies continuously evolve in the medical field. An outcomes report for an individual patient may guide a clinician in making therapy decisions that improve patient benefit and/or reduce medical costs. An outcomes report for a patient group being treated at a medical facility can lead to overall better performance by the facility as a whole in managing their patients and controlling medical costs.

Figure 8:
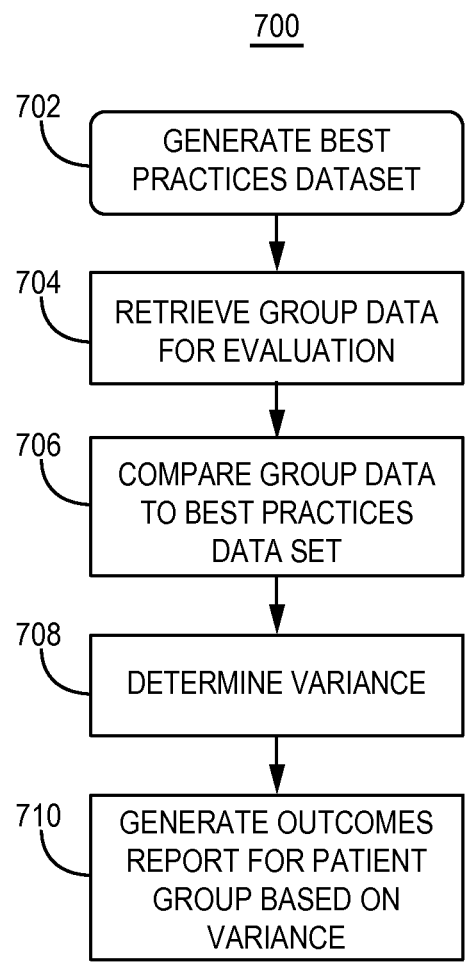
FIG. 8 is flow chart of another method for generating a predictive outcomes report for a group of patients.

FIG. 8 is flow chart 700 of a method for generating a predictive outcomes report for a patient group according to another example. At block 702, a best practices dataset is generated for a patient population. The best practices dataset includes IMD programming parameters and IMD therapy data and may include physiological data acquired by the IMD from electronic medical records or other sources. The central computer determines the best practices dataset from data stored in the central database for a group of patients that may be identified by the type of IMD, the patient diagnosis, or other common patient characteristic(s).

The best practices dataset may be determined from a population of patients having a common diagnosis and treatment modality. The population of patient may be identified as the patient records that form a matching dataset for a patient group under evaluation. The population of patients may alternatively be those patients for which a mathematical model has been generated representing a particular pattern or clustering of data.

From the population of patients, a subset of the population is selected as those patients within the population having a greatest improvement in a given outcome, which may be a symptom or condition, fewest side effects, fewest hospitalizations, or other "best" outcome or combination of outcomes. The best practices dataset may include physiological data, therapy data, and the "best" outcomes corresponding to the therapy data. For example, a population of patients may be identified as patients diagnosed with ventricular tachyarrhythmias and implanted with an ICD. The best practices subset may be selected as those patients having the lowest rate of shock delivery, e.g. the $10^{th}$ percentile of shock delivery frequency. These patients may be benefitting from optimally programmed therapy and/or tachyarrhythmia detection parameters that reduce the frequency of shocks through accurate rhythm detection and discrimination, delivery of anti-tachycardia therapies that preclude the necessity of shock delivery, and/or avoidance of unnecessary shocks. The best practices dataset may therefore include the programmed ICD parameters relating to tachyarrhythmia detection and/or therapy delivery.

Since the "best practices" will evolve over time, the best practices dataset may be updated periodically or whenever a threshold number of patients are added to the central database or new data is added for existing patients. The characteristics used to select a best practices subset of a particular patient population will vary between applications. Generally, patient data that represent the best responders to a particular therapy are identified for inclusion in a best practices dataset. The best responders may be identified based on one or more therapy outcomes or based on a lowest occurrence rate of adverse events.

After generating the best practices dataset, patient group data for evaluation is retrieved at block 704. The data for a patient group is evaluated by performing a comparative analysis of the group data and the best practices dataset at block 706. The group data undergoing evaluation may be all patients being treated by a given physician. In this way, a physician can determine how his/her practices compare to the best practices and if his/her patients are doing as well as the best practices dataset patient outcomes. In another example, the group data undergoing evaluation may be the data for all patients being treated at a particular medical facility having a common diagnosis and IMD. For example, all patients being treated at a particular cardiology clinic for ventricular tachyarrhythmia by having an ICD implanted may be compared to the best practices dataset obtained from data selected from all ventricular tachyarrhythmia patients having an ICD stored in the central database.

The comparative analysis made at block 706 may include comparing tachyarrhythmia episode detection and classification control parameters, therapy control parameters and therapy outcomes and/or occurrence rate of adverse events. For example, programmable tachyarrhythmia detection parameter settings may be compared and the number of shocks delivered may be compared between a group of patients for a given cardiology clinic and for a best practices dataset generated at block 702. Other examples of comparisons that may be made between an evaluation group and a best practices group may include comparing ventricular rate during AF episodes, comparing compliance with remote monitoring protocols, comparing frequency of office visits, hospitalizations, and/or emergency room visits or other patient-related, device-related, or patient care related parameters.

At block 708, variance of the data is determined. Variance of therapy control parameters may be determined within the group under evaluation and compared to variance within the best practices dataset. An overall variance of the group data and the best practices dataset may be determined as well. The variance will indicate how tightly the group data conforms to the best practices data. For example, a variance may indicate how widely a particular programmable therapy parameter setting is spread out among the group data as compared to the best practices data. The variance between the group data and the best practices dataset may be determined for one or more therapy control parameters.

An outcomes report is generated at block 710 based on the comparative analysis. The outcomes report may summarize how the group data deviates from or matches the best practices dataset. The report may indicate the variance of a therapy parameter(s) within the patient group. Some clinics may tightly manage all patients according to best practices and other clinics may have some but not all patients being managed according to the established best practices. The outcomes report can indicate how well the group data under evaluation matches the best practices dataset and how the group data outcome may change or improve if therapy changes are made to align the group therapy control parameters with those of the best practices dataset.

The report may indicate how many patients out of the group under evaluation meet the best practices for therapy and how many patients do not meet the best practices. In some cases, intentional variance from currently known best practices may exist. For example, a clinician may deliberately deviate from known best practices in attempting to test different therapy control parameters or combinations of parameters to gain further improvement in a given patient or group of patients. A clinic may be participating in a clinical trial to test different aspects of a therapy. In other cases, variance from currently known best practices may be random or unintentional, e.g. simply due to a lack of implementing the currently known best practices. Intentional variance from the best practices dataset may be identified in the report based on data included in the database for a given patient or group of patients.

The outcomes report may further include an economic analysis of costs of patient care. The average cost of care per patient included in the best practices dataset may be compared to the average cost of care for the group under evaluation and/or to the cost of care for each individual patient in the group. A cost savings analysis may be included in the outcomes report. For example, the cost of care due to an improved outcome that is correlated to a therapy practice may be determined such that a change in the cost of care for the group under evaluation may be predicted if the best practices are adopted for the group.

Figure 9:
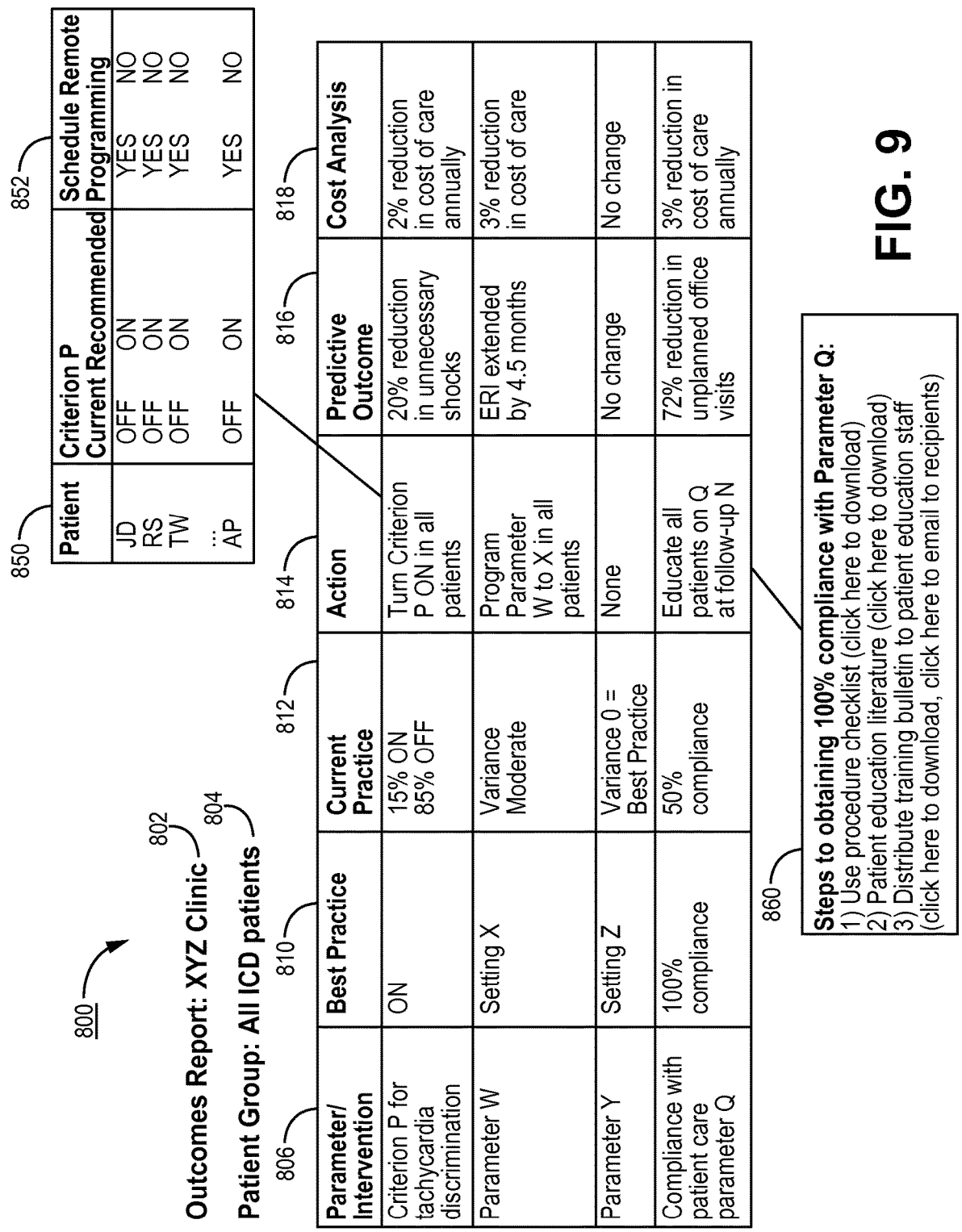
FIG. 9 is an example table that may be included in an outcomes report.

FIG. 9 is an example table 800 that may be included in an outcomes report generated by the central computer 150 and database 105 and transferred to a remote computer 152, 154 for viewing by a health care professional. As described in conjunction with FIG. 8, the central computer 150 and database 105 are configured to identify a best practice dataset having a most improved outcome for a given patient population. The best practice dataset is compared to a patient group under evaluation. The most improved outcome(s) identified for the best practice dataset may be a clinical or physiological outcome, a device performance outcome, or a monetary cost savings of medical care. The central computer 150 is configured to determine a therapy difference between the patient group and the best practice dataset having the most improved outcome, i.e. optimal actual outcome, and generate a report comparing the patient group and the best practice dataset. The report may include a recommended action to reduce the therapy difference, a predictive outcome if the recommended action is taken, and a cost difference if the recommended action is taken. Content that may be included in an example report is shown in FIG. 9.

The report may include table 800 that identifies the patient group under evaluation by characteristics or categories 802, 804. In this example, the patient group is identified by the medical facility or clinic 802 and the type of implanted device, e.g. as indicated by "All ICD patients" 804. In other examples, the patient group may be identified by a treating clinician, a clinical study, prescribed medications, surgical intervention, prescription drug, diagnosis, or any combination of thereof.

A best practice dataset is identified from the central database for all ICD patients having data stored in the database. The best practice dataset may be identified by searching the database for all patients having a characteristic matching the patient group 804 and having a clinical or device related outcome that is considered optimal. For example, all ICD patient data stored in the central database may be searched to identify the patients having the lowest occurrence of shock delivery and longest time to elective replacement indicator (ERI). A best practice dataset may include patients in a given percentile. For example, the best practice dataset may be all ICD patients in the fifth percentile for frequency of shocks delivered and in the ninety-fifth percentile for improvement in activities of daily living from before to after ICD implantation.

The IMD therapy control parameters and/or other therapy interventions of the best practice dataset are compared to the current therapy practice implemented in the patient group 804. The best practice dataset may represent key therapy control parameters programmed in an IMD that are correlated to the best outcomes used to select the best practice dataset. The best practice therapy control parameters may therefore not include a complete listing of all available programmable IMD parameters. For example, the best practice may be identified by a reduced number of programmed parameters listed in therapy/intervention column 806 and the associated best practice setting in column 810 that statistically correlates to positive outcomes in the best practice dataset.

The best practice dataset may additionally or alternatively be identified by therapy interventions other than programmed IMD parameters. Other therapy interventions have been listed above and may include operations performed by devices communicating with the IMD, surgical procedures, prescribed medications, and other patient care practices as described further below.

The current practice within the patient group 804 relative to the best practice (column 810) is listed in column 812 for each therapy parameter or intervention 806. The current practice 812 within the group 804 may be reported relative to the best practice 810 in different ways, depending in part on the type of therapy parameter being compared to the best practice 810. For example, if a programmable parameter or feature is programmed to simply be ON or OFF, the current practice may be indicated as the percentage of patients having the feature programmed according to the best practice setting. In other examples, a variance or range relative to a best practice setting may be reported or a percentage of patients in the group 804 meeting the best practice setting may be listed.

As an example, a rule or criterion, "Criterion P," used for discriminating between different types of tachycardia, e.g. supraventricular tachycardia (SVT) and ventricular tachycardia (VT) may be programmed ON or OFF. This criterion may require additional signal processing and analysis and may be programmed off in some patients to save processing power and time if the patient has not previously presented certain types of tachycardia, for example. However, the best practice may be to turn this feature ON, as indicated in the best practice column 810, resulting in the positive outcome of a reduction in the number of unnecessary cardioversion/defibrillation shocks. The current practice is reported in column 812 as the percentage of patient group 804 having the feature turned ON and the percentage having the feature turned OFF.

Criterion P may relate to rules or criterion for detecting AF for discriminating SVT from VT. For example, the central computer may determine that in all ICD patients having the AF criteria for tachycardia discrimination turned ON, the delivery of unnecessary shocks due to incorrect rhythm detection is significantly reduced compared to all patients having AF criteria turned OFF. Other examples of features that may be turned ON or OFF may include, without limitation, anti-tachycardia pacing (ATP) for atrial tachycardia, delivery of ATP during charging, tachycardia discrimination rules such as a sudden onset rules, sinus tachycardia detection criteria, wavelet morphology analysis or other ECG or EGM waveform morphology analysis and lead integrity analysis and alert functions.

The recommended action 814 for bringing the patient group 804 into full compliance with the best practice 810 is to turn Criterion P ON in all patients. The predictive outcome associated with this change is reported in column 816. The predictive outcome may be the outcome experienced by the best practices group.

Alternatively, the predictive outcome reported is computed specifically for group 804. In the example shown, a 20% reduction in unnecessary shocks is reported as the predictive outcome. This outcome may be computed by central computer 150 based on comparisons of an expected rate of unnecessary shocks if no change is made to Criterion P and the predicted rate of unnecessary shocks if the recommended action (shown in column 814) is taken. For example, the current rate of unnecessary shocks may be determined from the historical data stored for group 804. An expected reduction in the number of unnecessary shocks in the 85% of patients not receiving the best practice (shown in column 812) is computed. This expected reduction may therefore be a difference between a current rate of unnecessary shocks in the 85% of patients with Criterion P turned OFF and the rate of unnecessary shocks in the best practices group. No change in the rate of unnecessary shocks is expected in the 15% of patients already having the Criterion P feature turned ON. A predicted overall rate of unnecessary shocks is computed for the patient group 804 based on the current rate of unnecessary shocks in the 15% of patients with Criterion P turned ON and the predicted rate of unnecessary shocks in the other 85% of the patients if Criterion P is changed from OFF to ON. The difference between the current rate of unnecessary shocks and the predicted overall rate is reported in column 816. In this example, a 20% reduction in the occurrence of unnecessary shocks is predicted.

A cost analysis 818 associated with the predictive outcome 816 may additionally be computed and reported. Central computer 150 may be configured to compute a difference in the monetary cost of health care associated with the current practice 812 if the recommended action 814 is not taken as compared to the monetary cost of health care associated with the predictive outcome 816 if the recommended action 814 is taken to fully comply with the best practice 810 for a given therapy parameter or intervention 806. The cost difference may be a future cost savings (or expenditure) that is reduced (or increased) compared to current medical costs actually being incurred. Alternatively, the cost difference may be a future cost savings (or expenditure) expected based on a comparison of predicted medical costs if the action is not taken and predicted medical costs if the action is taken.

For example, by achieving a 20% reduction in the occurrence of unnecessary shocks in group 804, the overall cost of care for the entire group is expected to decrease by 2%. This cost analysis may be performed by using an average medical cost associated with an unnecessary shock determined from historical data and the total number of unnecessary shocks expected to be avoided annually based on the predicted 20% reduction. For example, costs of an unnecessary shock may include an office visit, an emergency room visit, ECG analysis etc. The cost reduction represents a savings which may be experienced for the entire group 804. Both the predictive outcome 816 and cost analysis 818 reflect the overall performance of the clinic or physician in managing the particular patient group 804 from both a disease management and cost management perspective.

In some examples, report 800 may include selectable cells that a user may select by clicking or hovering over the cell using a mouse or other pointing device or using a touch screen. Additional information, explanations, recommendations, or selectable actions may be displayed in a new or pop-up window. For example, links to research or clinical study reports pertaining to the best practice setting may be displayed when a user selects or hovers over the best practice cell in a given row of table 800. A list of patients and their current settings may be displayed by selecting a cell in current practice column 812. The cells in action column 814 may be selectable such that additional information and recommendations on how to achieve the best practice are displayed. Outcome rates or results may be reported for the best practice group and/or the evaluation group by selecting a cell in column 816. Other statistical data may be viewable by selecting a predictive outcome cell, such as the number of patients, mean, median, standard deviation, variance, statistical significance etc. Details relating to the cost analysis may be viewed by selecting a cell in column 818, such as actual dollar amounts, values used in making the cost analysis calculations, assumptions made, etc.

One example of such a pop-up window is shown in the offset table 850. Each patient in the evaluation group 804 having the Criterion P turned OFF (non-compliant with best practice) is listed. The recommended setting (ON) is listed. Table 850 includes a user selectable action 852. In some cases, the user may be able to select an action to remedy the current practice. In selecting the action, the centralized computer 150, database 105, remote computer 152, 154, and/or external medical device 130, 135, 140 (FIG. 1) are invoked to perform a function for bringing patient group 804 into compliance with the best practice. The function may be a scheduling function, a programming function, or generating an alert, notification, referral or other communication to a patient, physician or other medical personnel via network 110 or via cell phone, email or other communication means.

For example, a selectable action is listed in column 852 for scheduling remote programming to turn Criterion P on. The user may click on "yes" or "no" for each patient such that the next time a remote monitoring/programming session occurs, Criterion P will be adjusted to the best practices setting. A user may have a "select ALL" option to select "YES" or "NO" for all patients listed and may have the option to confirm a selection before implementing. It is recognized that patient safety and security precautions may be taken as appropriate for preventing an unauthorized user from making a programming change. In other examples, a selectable action may include scheduling an office visit, sending the patient a communication advising the patient to take a specific action(s), sending a message to a patient's electronic medical records file, or sending an action reminder to the physician or another medical care provider.

Other examples of therapy parameters 806 identified in the best practice dataset as having a best practice setting 810 correlated to an optimal outcome included in the table 800 include a programmable "Parameter W" having a best practice setting "X" and "Parameter Y" having a best practice setting of "Z". A programmable parameter may have a range of available settings, which may be numeric or non-numeric values and may relate to the detection of a treatable event or the therapy delivered in response to detecting a need for therapy. For example, programmable parameters that might be identified in a best practice dataset may include, without limitation, tachycardia and fibrillation detection intervals, the number of intervals required to detect a tachyarrhythmia, a shockable rhythm threshold interval, ECG or cardiac electrogram waveform morphology matching score, the rate or energy of an initial therapy delivered upon detection of a particular tachyarrhythmia, and timing intervals of a delivered therapy. In devices that are configured to deliver a pacing therapy, such as cardiac resynchronization therapy, programmable parameters may include pacing intervals, pacing sites, rate response control parameters, thresholds for detecting edema or other physiological conditions.

In the illustrative example, the current practice 812 for Parameter W is reported as having a "moderate" variance from the best practice setting X (column 810). The variance of a programmable parameter may be ranked, e.g. as low, moderate or high. A low variance may indicate a high percentage of patients are within a specified range of a programmable parameter setting, e.g. more than 80% of patients meet the best practice setting. A moderate variance may be defined as a current practice of sixty to eighty percent of patients meeting the best practice. Less than sixty percent of patients being treating according to the best practice setting may be indicated as a high variance. Numerous reporting methods may be conceived for indicating a variance of the current practice from a best practice for a given therapy parameter. The reporting methods used may be depend at least in part on the type of parameter being reported and the best practice setting. In other examples, the mean difference between current practice setting for group 804 and the best practice setting 810 may be reported in column 812. The range of current practice settings may be reported. Subsets of group 804 may be reported, such as n % of patients meet the best practice setting while m % are currently programmed with a setting that ranges from 20 to 80 units differently than the best practice setting, where the units may be ms, mV, Joules, or other unit or unitless depending on the programmable parameter.

The action 814 reported for Parameter W is to program Parameter W to a value of "X" in all patients, with a predicted outcome 816 of an elective replacement indicator (ERI) extended by an average of 4.5 months. The ERI is an indication of when the IMD should be replaced due to anticipated battery depletion at currently programmed settings. In this case the outcome is a device performance related outcome that does not significantly impact the quality or benefit of the therapy provided by the IMD other than to postpone the need for IMD replacement. The action cell in column 814 may be a selectable cell as described above to open a new window that lists all patients that are not meeting the best practice setting and a selectable action, such as scheduling a programming change to setting X.

A cost analysis comparing the ERI time at the current practice setting and the predicted ERI timing at the best practice setting can be performed to estimate a cost savings in the overall management of patient group 804. The cost savings is reported as 3% in this hypothetical example and is achieved by extending the average time to IMD replacement in patient group 804.

In another example, "Parameter Y" is reported to have a best practice setting "Z," and the current practice 812 within patient group 804 is reported to have zero variance from this setting, fully complying with the best practice setting. The recommended action 814 is none, with no change in the predictive outcome 816 and no change in the cost of care reported in the cost analysis column 818.

In some examples, a parameter/intervention 806 includes patient care practices such as in-office follow-up frequency, remote patient monitoring session compliance, patient and/or family or caregiver education, patient evaluation for device upgrade, and patient assessments with other specialists. Among the other specialists providing ancillary care that could have significant results on outcomes include dieticians, nutritionists, counselors, psychiatrists, physical therapists, occupational therapists, respiratory therapists, and so on. Patient care practices and/or clinic or patient compliance with these practices or resulting recommendations may be compared between a best practices group and the evaluation group.

For example, under parameter/intervention 806, "Compliance with patient care parameter Q" is listed with a compliance of 100% as the best practice 810. Compliance may be determined as a percentage of patients in compliance with a particular practice, such as the examples listed above. The compliance listed under current practice 812 of the evaluation group is 50%. A recommended action is listed in action column 814 to bring the evaluation group into 100% compliance with care parameter Q to achieve the predicted outcome 816 of a 72% reduction in unplanned office visits. An unplanned office visit is an office visit scheduled by the patient outside of a normal follow-up protocol. The cost analysis performed for this comparison and reported in column 818 may determine the difference between an average annual cost per patient in the patient group and a predicted average annual cost per patient reduced by the cost of 72% of unplanned office visits. The cost analysis performed is based on the predictive outcome reported which will vary between patient care practice parameters.

In an illustrative scenario, a patient care practice may include educating a patient who has received an implantable device on the importance of full compliance with the remote patient monitoring schedule. This education is consistently provided at the patient's one-week post-implant wound check in the best practice group. Current practice in the evaluation group may not include this education piece at the one-week post implant wound check, resulting in an overall reduced remote patient monitoring compliance. The user may select the action "Educate all patients on Q at follow-up N" to open a window recommending strategies toward achieving this result. In this example, recommended actions to bring this best practice into full compliance may include any of: integration of a procedure check list recommended for the one-week post-implant wound check; use of updated patient literature; distribution of a training communication or bulletin to appropriate clinic staff; and/or scheduling a staff training session. Some of these examples are shown in a sample pop-up window 860 that is displayed when the action cell is selected. In some embodiments, the pop-up window 860 includes user selectable actions, such as "click here" to download a procedure checklist, patient education literature, or staff training bulletin or to send an email to a list of appropriate recipients which may include relevant attachments such as a downloaded checklist, literature, or training bulletin.

In another example of a patient care practice parameter that may be listed in column 806, the patient care practice parameter Q may be patient assessment for an upgrade device six months prior to battery ERI (elective replacement indicator). Some patients may benefit from upgrading an ICD model that provides cardiac only for bradycardia to an ICD model including other pacing therapies such as cardiac resynchronization therapy (CRT). Other upgrades that add monitoring and/or therapy delivery features may better suit the patient's needs than the current IMD model. To promote appropriate selection of the subsequent device, a practice of evaluating 100% of patients in the clinic for individual device needs several months prior to device replacement may be recommended based on a best practice outcome.

Another patient care practice parameter example may be patient education during every annual follow-up on what to do if the patient receives a shock from an ICD. A "shock plan" may be reviewed by the medical professional, patient and family member or caregiver. An improved outcome resulting from reviewing a "shock plan" with all patients may include improved quality of life scores or other wellness assessments due to reduced anxiety. Another patient care parameter example is performing a psychosocial health assessment within two weeks of receiving an ICD shock. Some patients may experience anxiety subsequent to a shock and/or reduce their normal physical or social activity. A psychosocial assessment may be used to determine if the patient should be evaluated by a psychologist to address emotional or mental health issues.

In any of these examples, the best practice 810 and current practice 812 may be reported as a percentage of patients in full compliance with the patient care parameter. It is recognized that in order to evaluate outcomes of patient care practices and compare compliance with a given patient care practice, data entry indicating the completion of these practices is required in electronic medical records or other follow-up patient records that may be transferred to the central database 105 from data sources 160 (FIG. 1).

The action 814 recommended to achieve best practice compliance with a patient care parameter may vary depending on the particular patient care parameter. In some embodiments, selecting the action cell, in this example "Educate all patients on Q at follow-up N" may provide a pop-up display of detailed steps or recommendations for achieving the compliance goal with links to additional resources. Recommended actions may include automatic scheduling, specialist referral, automatic communication to patients and/or clinic staff, distributing education information or materials, automated phone call to patient to ensure home monitor is connected, automated communication (e.g. text message or email) to remind patients of their compliance schedule or other action to promote compliance with the best practice.

A clinic administrator or clinician can review a report such as that shown in Table 800 to compare the clinical practice at the clinic 802 or within the patient group 804 to the best practices used in a broader population of ICD patients or even worldwide as stored in the central database 105. By evaluating the recommended action 814 and possibly implementing this action in patient group 804, the clinical outcome can be improved and/or the cost of medical care can be reduced. It is recognized that in some cases the recommended action may not be appropriate in all patients and such action is taken into consideration by a practicing clinician along with other considerations to best meet patient need before necessarily implementing any change to the current practice.

While not shown explicitly in Table 800, a best practice dataset may include a surgical intervention, prescription medication dosage, or other therapeutic intervention as previously described in conjunction with FIG. 4. These other types of interventions can be listed in parameter/intervention column 806 with a corresponding best practice 810 identified by central computer 150. In some cases, such as in the case of a surgical intervention, the cost analysis may result in an increase in the cost of care, at least in the short term, but with an associated positive predictive outcome. The cost analysis 818 may therefore include a breakdown of short term and long term predictive cost analysis. For example, in the first year that a surgery is performed the cost analysis column 818 may report an increased cost of care associated with the surgery but anticipated reduced cost of care in the subsequent one or more years compared to the cost of care in patients not undergoing the surgery.

Table 800 is described based on a best practices analysis to identify a patient group having the best patient-related or device-related outcomes. The associated cost-analysis is performed as a secondary outcome. It is recognized that in alternative embodiments, the best practice group may be identified as a group having the lowest cost of care as primary outcome. As such, a best practices group may be identified as those patients having the lowest average annual cost of care while meeting some other minimum clinical outcome criteria such as a lack of a high-morbidity condition. For example, a best practices group may be all ICD patients at a single clinic having the lowest average annual patient care cost of all clinics represented in the database that are treating a predetermined minimum number of ICD patients and have a morbidity rate less than a high-morbidity threshold.

Thus, various embodiments of a system and method for evaluating and reporting patient outcomes have been described. However, one of ordinary skill in the art will appreciate that various modifications may be made to the described embodiments without departing from the scope of the claims. For example, although specific examples of therapies, outcomes, and reporting methods have been described, it is recognized that other therapies, outcomes, and reporting methods may be conceived depending at least in part on the type of medical condition being treated. These and other examples are within the scope of the following claims.

The invention claimed is:

1. A system, comprising:
a database coupled to a communication network and configured to store medical data for a plurality of patients received via the network from a plurality of data sources comprising data retrieved from implantable medical devices implanted in the plurality of patients;
a processor coupled to the database for accessing the stored medical data and configured to:
receive, from a remote computer, a request for a report of a predictive outcome of a therapy intervention for a patient group of at least one patient, the therapy intervention comprising a change in an operating parameter of an automated medical device, and, in response to the request:
generate a dataset from the stored medical data having at least one data characteristic matching a corresponding data characteristic of the patient group;
determine from the dataset at least one subset that had the therapy intervention take place subsequent to a time point that the at least one subset had the at least one matching data characteristic;
determine an outcome of the at least one subset;
produce the predictive outcome for the patient group based on the outcome of the at least one subset; and
transmit the report of the predictive outcome to the remote computer; and
automatically, in response to new data received by the database, produce an updated predictive outcome of the therapy intervention for the patient group and transmit an updated report of the updated predictive outcome to the remote computer.

2. The system of claim 1, wherein the outcome comprises a change in the performance of an implantable medical device.

3. The system of claim 1, wherein the outcome comprises a cost of medical treatment.

4. The system of claim 1, wherein the processor is further configured to:
generate a plurality of mathematical models of the data stored in the database; and
compare data of the patient group to the models to identify a dataset having the matching characteristic to the patient group.

5. The system of claim 1, wherein the processor is configured to:
determine a change in the at least one data characteristic of the patient group in response to the new data;
generate an updated dataset in response to determining the change; and
produce the updated predictive outcome in response to the updated dataset.

6. The system of claim 1, wherein the processor is configured to:
determine a change in an actual outcome of the dataset in response to the new data; and
produce the updated predictive outcome in response to the change in the actual outcome.

7. The system of claim 1, wherein the processor is further configured to:
determine from the dataset a subset having an optimal outcome;
determine a therapy intervention difference between the patient group data and the subset;
report an action to reduce the therapy intervention difference; and
report a predictive outcome expected if the reported action is taken.

8. The system of claim 7, wherein the processor is further configured to:
compute a predicted difference in a monetary cost of medical care if the reported action is taken; and
report the predicted change in the monetary cost of medical care.

9. The system of claim 1, wherein the outcome of the therapy intervention comprises at least one of a side-effect frequency, a hospitalization frequency, or a status of an atrial fibrillation (AF) burden of the patient group.

10. The system of claim 1, wherein the outcome of the therapy intervention comprises a change in a frequency of shocks delivered by the automated medical device.

11. The system of claim 1, wherein the change in the operating parameter of the automated medical device comprises a programming change made to the automated medical device.

12. A method, comprising:
receiving, by a database coupled to a communication network, medical data for a plurality of patients from a plurality of data sources comprising data retrieved from implantable medical devices implanted in the plurality of patients;
receiving, from a remote computer, a request for a report of a predictive outcome of a therapy intervention for a patient group of at least one patient, the therapy intervention comprising a change in an operating parameter of an automated medical device, and, in response to the request:
generating by a processor coupled to the database a dataset from the medical data having at least one data characteristic matching a corresponding data characteristic of the patient group of at least one patient;
determining from the dataset at least one subset that had the therapy intervention subsequent to a time point that the at least one subset had the at least one matching data characteristic;
determining an outcome of the at least one subset;
producing the predictive outcome for the patient group based on the outcome of the at least one subset; and transmitting the report of the predictive outcome to the remote computer; and automatically, in response to new data received by the database, producing an updated outcome of the therapy intervention for the patient group, and transmitting an updated report of the updated predictive outcome to the remote computer.

13. The method of claim 12, wherein the outcome comprises a change in the performance of an implantable medical device.

14. The method of claim 12, wherein the outcome comprises a cost of medical treatment.

15. The method of claim 12, further comprising:
generating a plurality of mathematical models of the data stored in the database; and
comparing data of the patient group to the plurality of models to identify the dataset having the matching characteristic to the patient group.

16. The method of claim 12, further comprising:
determining a change in the at least one data characteristic of the patient group in response to the new data;
generating an updated dataset in response to determining the change; and
producing the updated predictive outcome in response to the updated dataset.

17. The method of claim 12, further comprising:
determining a change in an actual outcome of the dataset in response to the new data; and
producing the updated predictive outcome in response to the change in the actual outcome.

18. The method of claim 12, further comprising:
determining from the dataset a subset having an optimal outcome;
determining a therapy difference between the patient group data and the subset;
reporting an action to reduce the therapy difference; and
reporting a predictive outcome expected if the reported action is taken.

19. The method of claim 18, further comprising:
computing a predicted difference in a monetary cost of medical care if the reported action is taken; and
reporting the predicted change in the monetary cost of medical care.

20. The method of claim 12, wherein the outcome of the therapy intervention comprises at least one of a side-effect frequency, a hospitalization frequency, or a status of an atrial fibrillation (AF) burden of the patient group.

21. The method of claim 12, wherein the outcome of the therapy intervention comprises a change in a frequency of shocks delivered by the automated medical device.

22. The method of claim 12, wherein the change in the operating parameter of the automated medical device comprises a programming change made to the automated medical device.

23. A system, comprising:
means for receiving medical data for a plurality of patients from a plurality of data sources comprising data retrieved from implantable medical devices implanted in the plurality of patients;
means for storing the received data;
means for receiving, from a remote computer, a request for a report of a predictive outcome of a therapy intervention for a patient group of at least one patient, the therapy intervention comprising a change in an operating parameter of an automated medical device, and, in response to the request:
generating a dataset from the medical data having at least one data characteristic matching a corresponding data characteristic of the patient group of at least one patient;
determining from the dataset at least one subset that had the therapy intervention subsequent to a time point that the at least one subset had the at least one matching data characteristic;
determining an outcome of the at least one subset;
producing the predictive outcome for the patient group based on the outcome of the at least one subset; and
transmitting the report of the predictive outcome to the remote computer; and
means for automatically, in response to new data received by the database, producing an updated outcome of the therapy intervention for the patient group, and transmitting an updated report of the updated predictive outcome to the remote computer.

24. A non-transitory computer readable storage medium storing a set of instructions to cause a system to:
receive by a database coupled to a communication network medical data for a plurality of patients from a plurality of data sources comprising data retrieved from implantable medical devices implanted in the plurality of patients;
receive, from a remote computer, a request for a report of a predictive outcome of a therapy intervention for a patient group of at least one patient, the therapy intervention comprising a change in an operating parameter of an automated medical device, and, in response to the request:
generate a dataset from the medical data having at least one data characteristic matching a corresponding data characteristic of the patient group of at least one patient;
determine from the dataset at least one subset that had the therapy intervention subsequent to a time point that the at least one subset had the at least one matching data characteristic;
determine an outcome of the at least one subset;
produce the predictive outcome for the patient group based on the outcome of the at least one subset; and
transmit the report of the predictive outcome to a remote computer; and
automatically, in response to new data received by the database, produce an updated predictive outcome of the therapy intervention for the patient group and transmit an updated report of the updated predictive outcome to the remote computer.

* * * * *